United States Patent
Yamaguchi et al.

(10) Patent No.: US 10,539,559 B2
(45) Date of Patent: Jan. 21, 2020

(54) PIVKA-II MEASUREMENT METHOD, MEASUREMENT REAGENT, AND MEASUREMENT KIT

(71) Applicants: FUJIREBIO INC., Tokyo (JP); SEKISUI MEDICAL CO., Ltd., Tokyo (JP)

(72) Inventors: Kentaro Yamaguchi, Tokyo (JP); Katsumi Aoyagi, Tokyo (JP); Azusa Terao, Tokyo (JP)

(73) Assignees: FUJIREBIO INC., Tokyo (JP); SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 14/420,122

(22) PCT Filed: Aug. 6, 2013

(86) PCT No.: PCT/JP2013/071188
§ 371 (c)(1),
(2) Date: Feb. 6, 2015

(87) PCT Pub. No.: WO2014/024853
PCT Pub. Date: Feb. 13, 2014

(65) Prior Publication Data
US 2015/0219638 A1    Aug. 6, 2015

(30) Foreign Application Priority Data
Aug. 9, 2012 (JP) ................................. 2012-176761

(51) Int. Cl.
| | | |
|---|---|---|
| *G01N 33/543* | (2006.01) | |
| *G01N 33/86* | (2006.01) | |
| *C07K 14/745* | (2006.01) | |
| *G01N 33/574* | (2006.01) | |

(52) U.S. Cl.
CPC ..... *G01N 33/54306* (2013.01); *C07K 14/745* (2013.01); *G01N 33/57438* (2013.01); *G01N 33/86* (2013.01); *G01N 2333/745* (2013.01)

(58) Field of Classification Search
None
See application file for complete search history.

(56) References Cited

U.S. PATENT DOCUMENTS

| | | | |
|---|---|---|---|
| 5,811,310 A | * | 9/1998 | Ghanbari et al. ............. 436/518 |
| 6,893,831 B1 | * | 5/2005 | Kanashima et al. ......... 435/7.94 |
| 2005/0113562 A1 | | 5/2005 | Teigelkamp et al. |

FOREIGN PATENT DOCUMENTS

| | | |
|---|---|---|
| EP | 0645630 A2 | 3/1995 |
| JP | 60-60557 A | 4/1985 |
| JP | 5-249108 A | 9/1993 |
| JP | 5-284994 A | 11/1993 |
| JP | 9-43237 A | 2/1997 |
| JP | 2000-235029 A | 8/2000 |
| JP | 2005-154440 A | 6/2005 |
| JP | 2007-192557 A | 8/2007 |

OTHER PUBLICATIONS

Walz et al., Radioimmunoassays for Human Prothrombin Fragments: Development and Implementation, Annals New York Academy of Sciences, 370(1), 398-413, 1981.*
International Search Report, issued in PCT/JP2013/071188, dated Sep. 3, 2013.

* cited by examiner

*Primary Examiner* — Andrea S Grossman
(74) *Attorney, Agent, or Firm* — Birch, Stewart, Kolasch & Birch, LLP

(57) ABSTRACT

Disclosed are a PIVKA-II measurement method that achieves better serum-plasma correlation than conventional methods, and a reagent and a kit therefor. The PIVKA-II measurement method according to the present invention comprises measuring PIVKA-II in a sample by an immunoassay using a mixture of an anti-F1 antibody that specifically binds to prothrombin fragment F1 or an antigen-binding fragment thereof and an anti-F2 antibody that specifically binds to prothrombin fragment F2 or an antigen-binding fragment thereof; and an anti-PIVKA-II antibody that specifically binds to PIVKA-II or an antigen-binding fragment thereof.

6 Claims, 1 Drawing Sheet
Specification includes a Sequence Listing.

(1) 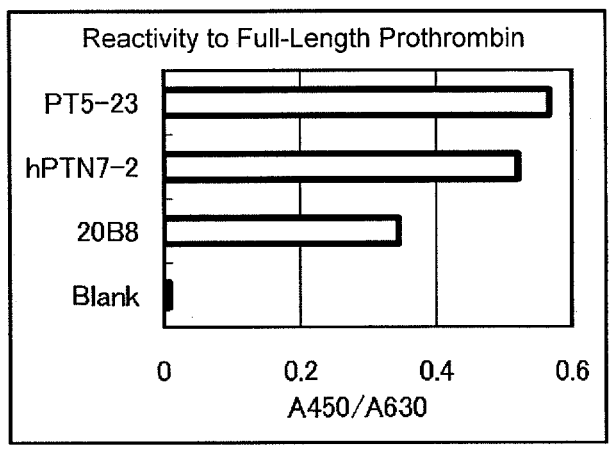
(2) 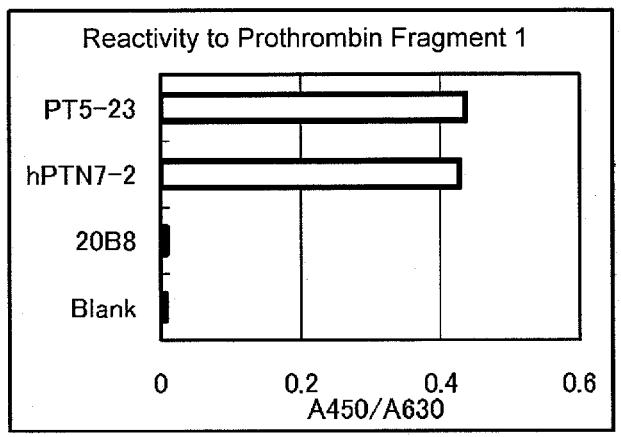
(3) 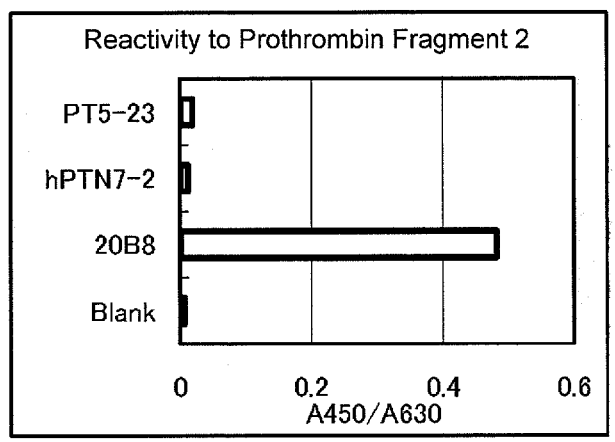

SEQUENCE LISTING

<160> NUMBER OF SEQ ID NOS: 2

<210> SEQ ID NO 1
<211> LENGTH: 622
<212> TYPE: PRT
<213> ORGANISM: Homo sapiens
<220> FEATURE:
<221> NAME/KEY: MOD_RES
<222> LOCATION: (49)..(49)
<223> OTHER INFORMATION: Gla or Glu
<220> FEATURE:
<221> NAME/KEY: MOD_RES
<222> LOCATION: (50)..(50)
<223> OTHER INFORMATION: Gla or Glu

```
<220> FEATURE:
<221> NAME/KEY: MOD_RES
<222> LOCATION: (57)..(57)
<223> OTHER INFORMATION: Gla or Glu
<220> FEATURE:
<221> NAME/KEY: MOD_RES
<222> LOCATION: (59)..(59)
<223> OTHER INFORMATION: Gla or Glu
<220> FEATURE:
<221> NAME/KEY: MOD_RES
<222> LOCATION: (62)..(62)
<223> OTHER INFORMATION: Gla or Glu
<220> FEATURE:
<221> NAME/KEY: MOD_RES
<222> LOCATION: (63)..(63)
<223> OTHER INFORMATION: Gla or Glu
<220> FEATURE:
<221> NAME/KEY: MOD_RES
<222> LOCATION: (68)..(68)
<223> OTHER INFORMATION: Gla or Glu
<220> FEATURE:
<221> NAME/KEY: MOD_RES
<222> LOCATION: (69)..(69)
<223> OTHER INFORMATION: Gla or Glu
<220> FEATURE:
<221> NAME/KEY: MOD_RES
<222> LOCATION: (72)..(72)
<223> OTHER INFORMATION: Gla or Glu
<220> FEATURE:
<221> NAME/KEY: MOD_RES
<222> LOCATION: (75)..(75)
<223> OTHER INFORMATION: Gla or Glu

<400> SEQUENCE: 1

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Xaa Xaa Val Arg Lys Gly Asn Leu Xaa Arg Xaa Cys Val Xaa Xaa Thr
    50                  55                  60

Cys Ser Tyr Xaa Xaa Ala Phe Xaa Ala Leu Xaa Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240
```

Gln Ala Lys Ala Leu Ser Lys His Gln Asp Phe Asn Ser Ala Val Gln
            245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
            275                 280                 285

Asn Tyr Cys Glu Glu Ala Val Glu Glu Glu Thr Gly Asp Gly Leu Asp
            290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
            325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
            355                 360                 365

Asp Ala Glu Ile Gly Met Ser Pro Trp Gln Val Met Leu Phe Arg Lys
            370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
            405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
            435                 440                 445

Ile His Pro Arg Tyr Asn Trp Arg Glu Asn Leu Asp Arg Asp Ile Ala
            450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
            485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
            515                 520                 525

Pro Ile Val Glu Arg Pro Val Cys Lys Asp Ser Thr Arg Ile Arg Ile
530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
            565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
            595                 600                 605

Leu Lys Lys Trp Ile Gln Lys Val Ile Asp Gln Phe Gly Glu
610                 615                 620

<210> SEQ ID NO 2
<211> LENGTH: 2018
<212> TYPE: DNA
<213> ORGANISM: Homo sapiens

<400> SEQUENCE: 2

```
gtcaggacag acaattcctc agtgacccag gagctgacac actatggcgc acgtccgagg      60
cttgcagctg cctggctgcc tggccctggc tgccctgtgt agccttgtgc acagccagca     120
tgtgttcctg gctcctcagc aagcacggtc gctgctccag cgggtccggc gagccaacac     180
cttcttggag gaggtgcgca agggcaacct ggagcgagag tgcgtggagg agacgtgcag     240
ctacgaggag gccttcgagg ctctggagtc ctccacggct acggatgtgt tctgggccaa     300
gtacacagct tgtgagacag cgaggacgcc tcgagataag cttgctgcat gtctggaagg     360
taactgtgct gagggtctgg gtacgaacta ccgagggcat gtgaacatca cccggtcagg     420
cattgagtgc cagctatgga ggagtcgcta cccacataag cctgaaatca actccactac     480
ccatcctggg gccgacctac aggagaattt ctgccgcaac cccgacagca gcaccacggg     540
accctggtgc tacactacag accccaccgt gaggaggcag gaatgcagca tccctgtctg     600
tggccaggat caagtcactg tagcgatgac tccacgctcc gaaggctcca gtgtgaatct     660
gtcacctcca ttggagcagt gtgtccctga tcggggcag cagtaccagg ggcgcctggc      720
ggtgaccaca catgggctcc cctgcctggc ctggccagc gcacaggcca aggccctgag      780
caagcaccag gacttcaact cagctgtgca gctggtggag aacttctgcc gcaacccaga     840
cggggatgag gagggcgtgt ggtgctatgt ggccgggaag cctggcgact ttgggtactg     900
cgacctcaac tattgtgagg aggccgtgga ggaggagaca ggagatgggc tggatgagga     960
ctcagacagg gccatcgaag ggcgtaccgc caccagtgag taccagactt tcttcaatcc    1020
gaggaccttt ggctcgggag aggcagactg tgggctgcga cctctgttcg agaagaagtc    1080
gctggaggac aaaaccgaaa gagagctcct ggaatcctac atcgacgggc gcattgtgga    1140
gggctcggat gcagagatcg gcatgtcacc ttggcaggtg atgctttttcc ggaagagtcc    1200
ccaggagctg ctgtgtgggg ccagcctcat cagtgaccgc tgggtcctca ccgccgccca    1260
ctgcctcctg tacccgcccct gggacaagaa cttcaccgag aatgaccttc tggtgcgcat    1320
tggcaagcac tcccgcacca ggtacgagcg aaacattgaa aagatatcca tgttggaaaa    1380
gatctacatc cacccaggt acaactggcg ggagaacctg gaccgggaca ttgccctgat    1440
gaagctgaag aagcctgttg ccttcagtga ctacattcac cctgtgtgtc tgcccgacag    1500
ggagacggca gccagcttgc tccaggctgg atacaagggg cgggtgacag gctggggcaa    1560
cctgaaggag acgtggacag ccaacgttgg taagggcag cccagtgtcc tgcaggtggt    1620
gaacctgccc attgtggagc ggccggtctg caaggactcc acccggatcc gcatcactga    1680
caacatgttc tgtgctggtt acaagcctga tgaagggaaa cgaggggatg cctgtgaagg    1740
tgacagtggg ggaccctttg tcatgaagag ccccttaac aaccgctggt atcaaatggg    1800
catcgtctca tggggtgaag gctgtgaccg ggatgggaaa tatggcttct acacacatgt    1860
gttccgcctaa agaagtggaa tacagaaggt cattgatcag tttggagagt aggggccac    1920
tcatattctg ggctcctgga accaatcccg tgaaagaatt atttttgtgt ttctaaaact    1980
atggttccca ataaaagtga ctctcagcga aaaaaaaa                             2018
```

PIVKA-II MEASUREMENT METHOD, MEASUREMENT REAGENT, AND MEASUREMENT KIT

TECHNICAL FIELD

The present invention relates to a PIVKA-II measurement method having excellent serum-plasma correlation, and an immunoassay reagent and kit for PIVKA-II.

BACKGROUND ART

PIVKA-II (Protein induced by vitamin K absence-II) is a glycoprotein having a structure similar to prothrombin, which is involved in blood coagulation. Prothrombin is a protein with 622 residues, and contains γ-carboxyglutamic acid (Gla) residues generated by γ-carboxylation of 10 glutamic acid (Glu) residues in the vicinity of the N-terminus. It is known that, during production of the prothrombin in the body, incomplete γ-carboxylation may occur due to lack of vitamin K, hepatic insufficiency, administration of a vitamin K antagonist, liver cell damage or the like, and glycoproteins in which all or part of the 10 residues are Glu residues may be found in blood. These proteins are PIVKA-II, which is also called abnormal prothrombin. Recently, detection of PIVKA-II at high concentration in plasma of patients with hepatocellular carcinoma has been reported, and PIVKA-II has begun to be used as a marker for monitoring diagnosis of hepatocellular carcinoma.

As a method for specifically detecting PIVKA-II in a sample, an immunoassay using both a monoclonal antibody that specifically recognizes PIVKA-II and a polyclonal antibody against prothrombin, one of which is an immobilized antibody and the other of which is a labeled antibody, has been reported (Patent Document 1).

In cases where a test substance in a blood-derived sample is measured, serum or plasma is mainly used. Depending on properties of the test substance, the assay system and the like, different measured values for the test substance may be obtained between the serum sample and the plasma sample in paired serum and plasma samples obtained from the same subject. That is, in some cases, the serum-plasma correlation is low and only one of the serum and plasma samples is applicable to the assay. This is especially problematic in cases where two test substances are measured at the same time. For example, in cases where two test substances are measured at the same time and one of the test substances can be measured only with serum, we may collect only a serum sample from the patient if the other test substance can be measured also with serum. However, in cases where the other test substance can be measured only with a plasma sample, both serum and plasma samples need to be collected from the patient. This increases the labor of the sample collection and treatment, as well as the burden on the patient. Thus, establishment of an assay system with high serum-plasma correlation has been demanded.

It is known that, also in measurement of PIVKA-II by ELISA using a monoclonal antibody that specifically recognizes PIVKA-II as an immobilized antibody and a polyclonal antibody against prothrombin as a secondary antibody, thrombin-reactive antibodies contained in the secondary antibody adversely affect the assay system for serum samples, resulting in unstable measured values (Patent Document 2). In order to solve this problem, Patent Document 2 reports that stable measurement of PIVKA-II can be attained even with a serum sample by using as a secondary antibody an antibody that does not react with human thrombin but specifically reacts with human prothrombin. However, in the method described in Patent Document 2, in order to remove antibodies against thrombin from the polyclonal antibody against human prothrombin, it is necessary to use a human prothrombin affinity column to obtain antibodies reactive with prothrombin and then to carry out dialysis, and further thereafter to use a human thrombin affinity column to obtain antibodies that are not reactive with thrombin and then to carry out dialysis. Thus, the antibody purification process is very complicated. Moreover, although the method of Patent Document 2 can also improve the serum-plasma correlation, its further improvement has been demanded. Furthermore, since polyclonal antibodies show variability among lots, monoclonal antibodies are generally more preferred than polyclonal antibodies for strictly securing the specificity. Although Patent Document 2 also describes use, in a PIVKA-II measurement method by ELISA, of a monoclonal antibody which does not react with human thrombin and is specifically reactive with human prothrombin, there is no description on the influence of use of such a monoclonal antibody on serum-plasma correlation, or problems caused by such use.

Patent Document 3 describes an immunoassay using both a monoclonal antibody that specifically recognizes PIVKA-II and a monoclonal antibody against prothrombin, one of which is used as an immobilized antibody and the other of which is used as a labeled antibody. The document also describes use of a mixture of PIVKA-II-specific monoclonal antibodies. However, Patent Document 3 originally does not describe the problem of serum-plasma correlation in the immunoassay system at all, and the influence of the method described in Patent Document 3 on serum-plasma correlation is not clear.

PRIOR ART DOCUMENTS

Patent Documents

Patent Document 1: JP S60-60557 A
Patent Document 2: JP H05-249108 A
Patent Document 3: JP H09-43237 A

SUMMARY OF THE INVENTION

Problems to be Solved by the Invention

An object of the present invention is to provide PIVKA-II measurement means having better serum-plasma correlation than conventional methods.

Means for Solving the Problems

The present inventors intensively studied on measurement of PIVKA-II, and, as a result, discovered that, by using as an antibody in an immunoassay an antibody mixture containing an antibody that specifically binds to human prothrombin fragment 1 and an antibody that specifically binds to human prothrombin fragment 2, the serum-plasma correlation is largely improved compared to conventional methods, thereby completing the present invention.

That is, the present invention provides a method for measuring PIVKA-II, comprising measuring PIVKA-II in a sample by carrying out an immunoassay using: a mixture of an anti-F1 antibody that specifically binds to prothrombin fragment F1 or an antigen-binding fragment thereof, and an anti-F2 antibody that specifically binds to prothrombin fragment F2 or an antigen-binding fragment thereof; and an anti-PIVKA-II antibody that specifically binds to PIVKA-II or an antigen-binding fragment thereof. The present invention also provides an immunoassay reagent for PIVKA-II in a sample, said reagent comprising: an anti-PIVKA-II antibody that specifically binds to PIVKA-II or an antigen-binding fragment thereof; an anti-F1 antibody that specifically binds to prothrombin fragment F1 or an antigen-binding fragment thereof; and an anti-F2 antibody that specifically binds to prothrombin fragment F2 or an antigen-binding fragment thereof. The present invention further provides an immunoassay kit for PIVKA-II in a sample, which kit comprises the immunoassay reagent of the above-described present invention.

Effect of the Invention

According to the present invention, a PIVKA-II measurement method which achieves excellent serum-plasma correlation, and an immunoassay reagent and kit for the method can be provided. Since the method of the present invention achieves much better serum-plasma correlation compared to conventional methods, the method of the present invention is more practical as a PIVKA-II measurement method.

BRIEF DESCRIPTION OF THE DRAWINGS

FIG. 1 is a graph illustrating the reactivities of the monoclonal antibodies prepared in Example 1 against full-length human prothrombin (1), F1 region (2), and F2 region (3).

MODE FOR CARRYING OUT THE INVENTION

Prothrombin contains the prothrombin fragment 1 (F1) region, the prothrombin fragment 2 (F2) region, and the thrombin region. PIVKA-II is a glycoprotein in which γ-carboxylation of 10 Glu residues in the vicinity of the N-terminus is incomplete and all or part of the 10 residues are therefore Glu without being converted into Gla. PIVKA-II also contains the prothrombin fragment 1 (F1) region, the prothrombin fragment 2 (F2) region, and the thrombin region.

The amino acid sequence of SEQ ID NO:1 is the amino acid sequence of PIVKA-II, in which the region of amino acid positions 44 to 198 corresponds to the prothrombin F1 region; and the region of amino acid positions 199 to 314 corresponds to the prothrombin F2 region. The region of amino acid positions 25 to 88, which contains part of the F1 region, is called the Gla region. In prothrombin, all of the 10 "Xaa"s in SEQ ID NO:1 are γ-carboxyglutamic acid (Gla) residues. This prothrombin sequence is deposited in GenBank under Accession No. NP_000497. The base sequence of SEQ ID NO:2 is a sequence encoding PIVKA-II of SEQ ID NO:1 and prothrombin of NP_000497, and deposited in GenBank under Accession No. NM_000506. The region of base positions 44 to 1912 in SEQ ID NO:2 is the coding region.

In the measurement method of the present invention, a mixture of an anti-F1 antibody and an anti-F2 antibody; and an anti-PIVKA-II antibody which specifically binds to PIVKA-II; are used to perform a sandwich immunoassay. By using the mixture of an anti-F1 antibody and an anti-F2 antibody as one of the antibodies in the sandwich method, the serum-plasma correlation in the measured value of PIVKA-II can be preferably improved.

The anti-F1 antibody is an antibody that specifically binds to prothrombin F1. That is, the anti-F1 antibody is an antibody whose epitope is present in the prothrombin F1 region of PIVKA-II and which recognizes the epitope to bind to PIVKA-II. For example, when an antibody binds only to the F1 region fragment of prothrombin or PIVKA-II and does not substantially bind either to the F2 region fragment or to the thrombin region fragment, the antibody is an "antibody that specifically binds to prothrombin F1" whose epitope is present in the F1 region. The term "does not substantially bind" herein means that the antibody does not bind either to the F2 region fragment or to the thrombin region fragment at a detectable level (that is, the levels of binding to the F2 region fragment and binding to the thrombin region fragment are below the background level), or that, even if the bindings occur at detectable levels, the levels of binding to these fragments are apparently lower than the level of binding to the F1 region fragment so that it is clear for those skilled in the art that the antibody binds to neither the F2 region fragment nor the thrombin region fragment. The anti-F1 antibody may be an antibody capable of binding to both the F1 region of PIVKA-II and the F1 region of prothrombin, and does not need to have the specificity to PIVKA-II molecules (i.e. the binding property with which the antibody does not bind to prothrombin and binds only to PIVKA-II).

The anti-F2 antibody is an antibody which specifically binds to prothrombin F2. That is, the anti-F2 antibody is an antibody whose epitope is present in the prothrombin F2 region of PIVKA-II and which recognizes the epitope to bind to PIVKA-II. For example, when an antibody binds only to the F2 region fragment of prothrombin or PIVKA-II and does not substantially bind either to the F1 region fragment or to the thrombin region fragment, the antibody is an "antibody that specifically binds to prothrombin F2". The term "does not substantially bind" herein means that the antibody does not bind either to the F1 region fragment or to the thrombin region fragment at a detectable level (that is, the levels of binding to the F1 region fragment and the thrombin region fragment are below the background level), or that, even if the bindings occur at detectable levels, the levels of binding to these fragments are apparently lower than the level of binding to the F2 region fragment so that it is clear for those skilled in the art that the antibody binds to neither the F1 region fragment nor thrombin region fragment. Since the amino acid sequence of the F2 region is identical between PIVKA-II and prothrombin, the anti-F2 antibody is usually an antibody capable of binding both to the F2 region of PIVKA-II and to the F2 region of prothrombin.

The anti-PIVKA-II antibody is an antibody that binds only to PIVKA-II, and does not substantially binds to prothrombin.

Each of the anti-F1 antibody, anti-F2 antibody, and anti-PIVKA-II antibody may be a monoclonal antibody or polyclonal antibody. In view of reproducibility of the immunoassay etc., a monoclonal antibody may be preferably used. Each of these antibodies may also be used in the form of an antibody fragment (antigen-binding fragment) retaining the binding capacity to the corresponding antigen.

Methods for preparing polyclonal antibodies, monoclonal antibodies, and antigen-binding fragments per se are well-known conventional methods, and the anti-F1 antibody, anti-F2 antibody, anti-PIVKA-II antibody, and their antigen-binding fragments can be prepared according to the conventional methods. These antibodies are also commercially available, and commercially available antibodies may be used.

The anti-F1 polyclonal antibody can be obtained by, for example, immunizing an animal (excluding human) with the F1 polypeptide or its partial fragment using, if necessary, an adjuvant, and then obtaining an antiserum from blood collected from the animal, followed by purifying a polyclonal antibody in the antiserum. Normally, in order to increase the antibody titer in the immunized animal, the immunization is carried out a plurality of times for several weeks. The antibody in the antiserum can be purified by, for example, fractionation by ammonium sulfate precipitation or anion chromatography, or affinity column purification. The anti-F2 polyclonal antibody can be similarly prepared using the F2 polypeptide or its partial fragment as an immunogen.

The anti-F1 monoclonal antibody can be prepared by, for example, the well-known hybridoma method. More specifically, the monoclonal antibody can be obtained by: immunizing an animal (excluding human) with the F1 polypeptide (F1 region fragment), prothrombin, PIVKA-II, or a partial fragment thereof using, if necessary, an adjuvant; collecting antibody-producing cells such as spleen cells or lymphocytes from the animal; fusing these cells with myeloma cells to prepare hybridomas; selecting a hybridoma producing an antibody that binds to the F1 polypeptide; growing the hybridoma; and then obtaining an anti-F1 monoclonal antibody from the culture supernatant. The anti-F2 monoclonal antibody can be similarly prepared by using the F2 polypeptide, prothrombin, PIVKA-II, or a partial fragment thereof as an immunogen and selecting a hybridoma producing an antibody that binds to the F2 polypeptide.

As for the anti-PIVKA-II antibody, a polyclonal antibody can be prepared using a partial Gla region fragment with incomplete carboxylation as an immunogen. However, since sufficient specificity to PIVKA-II is required in the present invention, a monoclonal antibody is typically used. The PIVKA-II monoclonal antibody can be prepared by using PIVKA-II or its partial fragment (partial fragment containing at least a part of the 10 residues in the Gla region that undergoes carboxylation) as an immunogen to prepare hybridomas, selecting a hybridoma producing an antibody that binds to PIVKA-II but does not bind to prothrombin, and then collecting the antibody. Specific examples of the method for producing an anti-PIVKA-II antibody include the methods described in JP S60-60557 A and JP H09-249699 A.

The "antigen-binding fragment" may be any antibody fragment as long as the fragment retains the binding capacity (antigen-antibody reactivity) to the corresponding antigen of the original antibody. Specific examples of the antigen-binding fragment include, but are not limited to, Fab, F(ab')$_2$, and scFv. As is well known, Fab and F(ab')$_2$ can be obtained by treating a monoclonal antibody with a protease such as papain or pepsin. The method for preparing scFv (single chain fragment of variable region; single-chain antibody) is also well known. For example, scFv can be obtained by: extracting mRNA of a hybridoma prepared as described above; preparing single-stranded cDNA; performing PCR with primers specific to the immunoglobulin H-chain and L-chain to amplify the immunoglobulin H-chain gene and L-chain gene; ligating the amplified products using a linker; giving an appropriate restriction site to the resulting product; introducing the product into a plasmid vector; transforming *E. coli* with the resulting vector to allow expression of scFv; and then collecting the expressed scFv from the *E. coli*.

The polypeptide or its partial fragment to be used as the immunogen can be prepared by a conventional method such as chemical synthesis, genetic engineering techniques or the like. The polypeptide or its partial fragment can also be obtained by extracting and purifying prothrombin or PIVKA-II from fresh human plasma or the like (see, for example, Thromb. Diath. Haemorph. 1966; 16:469-90).

Specific examples of the chemical synthesis method include the Fmoc method (fluorenylmethyloxycarbonyl method) and tBoc method (t-butyloxycarbonyl method). The synthesis may also be carried out by a conventional method using a commercially available peptide synthesizer of every kind. In cases of the chemical synthesis, a desired polypeptide can be synthesized based on the amino acid sequence alone.

Methods for preparing a polypeptide by genetic engineering techniques are also well known. More specifically, for example, the polypeptide can be prepared as follows. First, RNA is extracted from human-derived cultured cells or the like, and reverse transcription is carried out to synthesize cDNA from mRNA. Using this cDNA as a template and using primers designed based on mRNA sequence information of human prothrombin, PCR is carried out to prepare a polynucleotide encoding full-length prothrombin or a desired portion (F1 region, F2 region or the like) thereof. The primers to be used in the PCR can be designed as appropriate based on the base sequence of SEQ ID NO:2, base sequence information of human prothrombin deposited in a database such as GenBank, or the like. A polynucleotide encoding a desired polypeptide can also be prepared by a conventional method using a commercially available nucleic acid synthesizer. Since the codons encoding each amino acid are known, if an amino acid sequence can be specified, the base sequence of a polynucleotide encoding the amino acid sequence can be determined. Thereafter, the prepared polynucleotide may be incorporated into an appropriate vector to allow expression of the polypeptide by an appropriate expression system, and the expressed polypeptide may be collected to obtain the desired polypeptide. Vectors and expression systems (bacterial expression systems, yeast cell expression systems, mammalian cell expression systems, insect cell expression systems, cell-free expression systems, and the like) that may be used herein are well known, and various vectors, host cells, reagents, and kits are commercially available. Therefore, those skilled in the art can select and use appropriate ones. Human-derived cultured cells are also commercially available or distributed, and can be easily obtained.

The mixing ratio between the anti-F1 antibody and the anti-F2 antibody is not limited as long as the ratio is within the range where good serum-plasma correlation can be obtained for measured values of PIVKA-II. Especially good serum-plasma correlation can be obtained at a mixing ratio of anti-F1 antibody:anti-F2 antibody=1:0.2-2, preferably 1:0.3-1.5, more preferably 1:0.5-1.0. As described in the Examples below, in cases where only the anti-F2 antibody is used, the measured values of PIVKA-II for the plasma samples are higher than the measured values for the serum samples, and good serum-plasma correlation cannot be obtained. In cases where only the anti-F1 antibody is used, the measured values of PIVKA-II for the serum samples are higher than the measured values for the plasma samples, and good serum-plasma correlation cannot be obtained. By using a mixture of the anti-F1 antibody and the anti-F2 antibody, serum-plasma correlation can be improved.

Sandwich immunoassay per se is a well-known method. Specific examples of sandwich immunoassay include chemiluminescent enzyme immunoassay (CLEIA), Enzyme-Linked ImmunoSorbent Assay (ELISA), radioimmunoassay, and electrochemiluminescence immunoassay. Any of these various methods may be used in the present invention.

In the sandwich assay system, one of two kinds of antibodies is immobilized on a solid phase to provide an immobilized antibody, and the other is provided as a labeled antibody. In the present invention, an anti-F1 antibody/anti-F2 antibody mixture is used as one kind of antibody, and an anti-PIVKA-II antibody is used as the other kind of antibody. Either of these may be used as the immobilized antibody. In the Examples below, an anti-PIVKA-II antibody is used as the immobilized antibody, and an antibody mixture is used as the labeled antibody. However, the present invention is not limited thereto.

The method for measuring PIVKA-II of the present invention is concretely described below by way of an example in which an anti-F1 antibody/anti-F2 antibody mixture is used as the labeled antibody. First, a PIVKA-II antibody (immobilized antibody) is immobilized on a carrier. The immobilized PIVKA-II antibody is brought into contact with PIVKA-II contained in a sample to allow specific binding between the immobilized antibody and PIVKA-II. Subsequently, unbound components in the sample are removed by, for example, washing of the carrier with an appropriate buffer, and an anti-F1 antibody/anti-F2 antibody mixture labeled with a labeling substance (that is, a mixture of a labeled anti-F1 antibody and a labeled anti-F2 antibody) is allowed to bind to the PIVKA-II bound to the immobilized antibody. After completion of the reaction, unreacted components are removed by, for example, washing of the carrier with an appropriate buffer, and a signal from the labeling substance is detected by an appropriate method. By this, PIVKA-II contained in the sample can be measured.

The solid phase is not limited, and may be the same as a solid phase used in a known sandwich immunoassay system. Specific examples of the material of the solid phase include, but are not limited to, polystyrene, polyethylene, and Sepharose. Physical properties of the solid phase are essentially not important. The solid phase to be used is preferably such one that allows easy immobilization of an antibody on the surface, and also allows easy separation of the immune complex formed during the assay from unreacted components. The solid phase is especially preferably a plastic plate or magnetic particles used in conventional immunoassays. From the viewpoints of ease of handling, storage, separation and the like, magnetic particles composed of the above-described material are most preferably used. The antibody can be bound to such a solid phase by a method well known to those skilled in the art.

The labeling substance is also not limited, and may be the same as one used in a known immunoassay system. Specific examples of the labeling substance include enzymes, fluorescent substances, chemiluminescent substances, staining substances, and radioactive substances. Examples of the enzymes that may be used include, but are not limited to, known enzymes such as alkaline phosphatase (ALP), peroxidase, and β-galactosidase. For providing an assay system having high detection sensitivity, ALP is preferably used.

In cases where an enzyme is used as the labeling substance, an object to be measured can be measured by allowing a substrate corresponding to the enzyme, such as a coloring substrate, fluorescent substrate or luminescent substrate, to react with the enzyme, and measuring a signal consequently generated to determine the enzyme activity. For example, in cases where ALP is used as the labeling substance, a luminescent substrate such as disodium 3-(4-methoxyspiro(1,2-dioxetane-3,2'-tricyclo[3.3.1.13,7]decan)-4-yl)phenylphosphate (e.g., trade name AMPPD) may be used.

In cases where biotin or hapten is used as the labeling substance, the measurement may be carried out using streptavidin, hapten antibody or the like to which an enzyme, fluorescent substance, chemiluminescent substance, staining substance, or radioactive substance is bound.

The means for detecting the signal is appropriately selected depending on the type of the labeling substance. For example, a colorimeter or absorptiometer may be used in cases where the signal is coloring; a fluorometer may be used in cases of fluorescence; a photon counter may be used in cases of luminescence; and a radiation meter may be used in cases of radiation. PIVKA-II in a sample can be quantified by preliminarily measuring PIVKA-II in standard samples containing PIVKA-II at known concentrations by the method of the present invention and plotting the correlation between the amount of signal from the label and the PIVKA-II concentration in each standard sample to prepare a calibration curve, followed by carrying out the same measurement operation for the sample whose PIVKA-II concentration is unknown to measure the amount of signal from the label and then applying the measured value to the calibration curve.

The sample to which the method of the present invention is applied is a sample separated from a subject, and the sample is preferably a blood sample, especially preferably plasma or serum. By the measurement method of the present invention, PIVKA-II can be stably measured for either a plasma sample or serum sample. The sample may be diluted as required before use.

The present invention also provides an immunoassay reagent for PIVKA-II in a sample, which reagent contains: an anti-PIVKA-II antibody or an antigen-binding fragment thereof (anti-PIVKA-II antibody or the like); an anti-F1 antibody or an antigen-binding fragment thereof (anti-F1 antibody or the like); and an anti-F2 antibody or an antigen-binding fragment thereof (anti-F2 antibody or the like). In the immunoassay reagent, the anti-F1 antibody or the like and the anti-F2 antibody or the like may be packed separately in containers, or may be preliminarily mixed together and packed in a container as a mixture. The reagent may further contain one or more other components useful for e.g. stabilization of the antibodies or antigen-binding fragments thereof. The antibodies or antigen-binding fragments thereof may be in the form of being labeled with a labeling substance, or in the form of being immobilized on a solid phase such as a plate or particles.

The immunoassay reagent may be appropriately combined with one or more of other reagents and the like to be provided as a kit for immunoassay of PIVKA-II in a sample. The other reagents required for immunoassay are well known.

Examples of the reagents that may be further contained in the kit of the present invention besides the above-described immunoassay reagent include a sample dilution liquid, washing liquid, and, in cases where the labeling substance used in the labeled antibody is an enzyme, a substrate solution for the enzyme.

EXAMPLES

The present invention is concretely described below by way of Examples.

However, the present invention is not limited to these Examples and the like.

Example 1. Preparation of Labeled Antibodies (A) Preparation of Hybridomas

Purified prothrombin (purified from fresh human plasma according to the method described in Shapiro S. et al., The purification of human prothrombin. Thromb. Diath. Haemorph. 1966; 16:469-90) was diluted with 10 mM phosphate buffer (pH 7.3) supplemented with 0.15 M NaCl such that the final concentration of the purified prothrombin was 0.2 to 1.0 mg/mL, and mixed with an equal amount of Freund's complete adjuvant to provide a water-in-oil emulsion. The emulsion was intraperitoneally administered to a BALB/c mouse of 7 weeks old, and similar immunization was carried out 2 or 3 times at 2-week intervals thereafter using Freund's incomplete adjuvant instead of Freund's complete adjuvant. About 2 weeks thereafter, 100 µL of 0.2 to 1.0 mg/mL purified prothrombin dissolved in physiological saline was intraperitoneally administered (final booster).

On Day 3 after the final booster, the spleen was aseptically removed from the immunized animal, and cut into sections using scissors. The spleen cells were then dispersed into individual cells using a mesh, and washed 3 times with RPMI-1640 medium, followed by counting of the cell number. Cells of a mouse myeloma cell line P3X63Ag8-U1 in the logarithmic phase were washed in the same manner as described above, and the cell number was adjusted to 1 to 1/10 of the measured number of spleen cells. These cells were placed in a 50-ml centrifuge tube, and mixed together. Centrifugation was carried out at 200×g for 5 minutes, and the supernatant was then removed, followed by adding 1 ml of polyethylene glycol (PEG) 1500 (manufactured by Merck) to the cells to allow cell fusion. Thereafter, 15 ml of RPMI-1640 medium was added thereto for dilution of polyethylene glycol.

The fused cells were centrifuged (200×g, 5 minutes) to remove PEG, and cultured for about 10 days in RPMI-1640 medium supplemented with 10% fetal bovine serum, hypoxanthine, aminopterin and thymidine (HAT) using a 96-well plate, to allow growth of only hybridomas. Thereafter, aliquots of the culture supernatants were collected, and screening of wells each producing prothrombin antibody was carried out by the ELISA method using purified prothrombin as an immobilized antigen, to obtain a plurality of hybridomas each producing a monoclonal antibody having reactivity against prothrombin. The obtained hybridomas were treated by the ordinary limiting dilution method to obtain single clones.

(B) Preparation of Monoclonal Antibodies

About $1 \times 10^7$ cells of each hybridoma obtained by the method described in (A) were transplanted to the abdominal cavity of each mouse to which 0.5 mL of pristane was preliminarily intraperitoneally administered, and the monoclonal antibodies produced into the ascites were obtained. Each monoclonal antibody was purified by separating the IgG fraction using a Protein A-conjugated Sepharose column (manufactured by Bio-Rad).

Subsequently, each of the prothrombin polypeptide, F1 polypeptide, and F2 polypeptide was immobilized on a microtiter plate, and the obtained monoclonal antibodies were investigated for the reactivity against each polypeptide. That is, full-length prothrombin (Termo), prothrombin-fragment 1 (Haematologic Technologies Inc.), and prothrombin-fragment 2 (Haematologic Technologies Inc.) were diluted with 0.1 M phosphate buffer (pH 7.0), respectively, to prepare 5 µg/mL solutions. To the wells of a microtiter plate (Nunc, Maxisorp), 100 µL of any one of these antigen solutions was added, and the reaction was allowed to proceed at 4° C. for 12 to 18 hours. The antigen solutions were then removed, and 300 µL of 50 mM Tris-HCl buffer (pH 7.2) supplemented with 1% BSA and 0.1% sodium azide was added to each well. The resulting mixture was left to stand at room temperature for 2 hours, and unreacted portions in the microplate were blocked, followed by 3 times of washing using 10 mM Tris-HCl (pH 7.2) supplemented with 0.01% Triton X-100 and 0.03 M NaCl (hereinafter referred to as washing liquid), to obtain a plate on which the peptides were immobilized. After preparing 5 µg/mL antibody solutions of monoclonal antibodies hPTN7-2, PT5-23 and 20B8, 100 µL of any one of antibody solutions was added to the wells of the microplate on which the 3 kinds of polypeptides described above (full-length prothrombin, prothrombin-fragment 1, and prothrombin-fragment 2) were immobilized. The reaction was allowed to proceed at room temperature for 1 hour, and the antibody solutions were then discarded, followed by washing the wells 3 times with the washing liquid. To each well, 100 µL of alkaline phosphatase-labeled anti-mouse IgG (manufactured by Jackson ImmunoResearch Inc.) diluted to a predetermined concentration was added, and the reaction was allowed to proceed at room temperature for 1 hour. The solution of the labeled antibody was discarded, and washing was performed 3 times with the washing liquid, followed by adding 100 µL of 1 M diethanolamine-hydrochloride buffer (pH 10.5) supplemented with 10 mM 4-nitrophenylphosphoric acid as a coloring substrate and 1 mM magnesium chloride to each well to perform coloring reaction. The resulting mixture was left to stand in the dark at room temperature for 15 minutes, and 100 µL of 0.1 M phosphate buffer (pH 7.0) supplemented with 50 mM EDTA was added thereto to stop the reaction, followed by measuring the absorbances at 450 nm/630 nm using a microplate reader (manufactured by Bio-Rad).

The results of the measurement are shown in FIG. 1. Since the monoclonal antibodies hPTN7-2 and PT5-23 reacted with the prothrombin peptide and the F1 polypeptide, but did not react with the F2 polypeptide, these antibodies could be confirmed to be anti-F1 monoclonal antibodies that specifically recognized F1. On the other hand, since the monoclonal antibody 20B8 reacted with the prothrombin polypeptide and the F2 polypeptide, but did not react with the F1 polypeptide, the antibody could be confirmed to be an anti-F2 monoclonal antibody that specifically recognized F2.

(C) Preparation of Labeled Antibodies

Subsequently, 6 mL of 3 mg/mL hPTN7-2 antibody solution was applied to a G-25 column (manufactured by Pharmacia) equilibrated with 0.1 M citrate buffer (pH 3.5) to replace the buffer of the antibody solution. About 100 jut of 1 mg/mL pepsin solution was added to the solution, and the resulting mixture was then left to stand at 37° C. for 1 hour. The pH of the solution was adjusted to near neutral with Tris buffer, and the solution was then applied to a Superdex 200 column (manufactured by Pharmacia) to carry out purification of the antibody by gel filtration. A single peak at an absorbance of 280 nm in the obtained fraction was pooled to provide the hPTN7-2 antibody F(ab')$_2$ fragment. To 4 mL of the F(ab')$_2$ fragment solution, 200 µL of 0.2 M 2-mercaptoethylamine (hereinafter referred to as 2-MEA) solution was added, and the resulting mixture was left to stand at 37° C. for 2 hours to carry out reduction treatment. The mixture was then applied to a G-25 column to remove 2-MEA, to provide the hPTN7-2 antibody Fab' fragment.

To G-25 equilibrated with 0.1 M phosphate buffer (pH 7.0), 1.5 mL of 10 mg/mL high-specific-activity ALP solution was applied to replace the buffer of the ALP solution. To the resulting solution, 70 µL of a solution of 10 mg/mL N-(4-maleimidobutyryloxy)-succinimide (hereinafter referred to as GMBS) in dimethylformamide was added, and the resulting mixture was left to stand at 30° C. for 1 hours to allow the reaction to proceed. The solution was then applied to a G-25 column equilibrated with 0.1 M phosphate buffer (pH 6.3) to remove excessive GMBS, thereby preparing maleimidated ALP. Four milliliters of the preliminarily prepared hPTN7-2 antibody Fab' fragment solution and 3 mL of the maleimidated ALP solution were mixed with 13 mL of 0.1 M phosphate buffer (pH 6.3), and the resulting mixture was left to stand at room temperature for 1 hour to prepare an ALP-labeled antibody. To this antibody, 1 mL of 2 M 2-MEA solution was added, and the resulting mixture was left to stand at room temperature for 30 minutes to block excessive maleimide groups, followed by applying the resulting solution to a Superdex 200 column to carry out purification. Among the peaks found at an absorbance of 280 nm, a peak at a molecular weight where the ratio between Fab' and ALP was 1:1 was pooled to provide a purified ALP-labeled hPTN7-2 antibody (ALP-labeled anti-F1 antibody). The PT5-23 antibody and the 20B8 antibody were treated in the same manner to provide a purified ALP-labeled PT5-23 antibody (ALP-labeled F1 antibody) and a purified ALP-labeled 20B8 antibody (ALP-labeled anti-F2 antibody).

Example 2. Measurement Data (D) Measurement of PIVKA-II

As samples, paired samples of human serum and plasma (heparin sodium and disodium EDTA) each obtained from the same healthy subject were used. The measurement was carried out using, in addition to the enzyme-labeled antibodies, reagents (antibody-binding particles and washing liquid) included in Lumipulse Presto PIVKA-II Eisai (manufactured by Fujirebio Inc.).

First, 20 µL of the sample was added to 50 µL of antibody-binding particles conjugated with an anti-PIVKA-II monoclonal antibody (mouse) (anti-PIVKA-II monoclonal antibody (mouse)-conjugated ferrite particles) which specifically bound to PIVKA-II, and the resulting mixture was stirred, followed by allowing the reaction to proceed at 37° C. for 8 minutes. The residual reaction liquid was removed from the magnetic particles by separation using magnetic force, and the particles were washed with the washing liquid. To the washed particles, an ALP-labeled anti-F1 antibody (hPTN7-2 antibody or PT5-23 antibody) prepared in (C) (final concentration, 0.4 µg/mL) and the ALP-labeled anti-F2 antibody (final concentration, 0.2 µg/mL) were added, and the resulting mixture was stirred, followed by allowing the reaction to proceed at 37° C. for 8 minutes. For Comparative Example, an ALP-labeled anti-prothrombin polyclonal antibody was used as the enzyme-labeled antibody.

Thereafter, the residual reaction liquid was removed again from the magnetic particles by separation using magnetic force, and the particles were then washed with the washing liquid. To these particles, 200 µL of a substrate liquid containing 3-(2'-spiroadamantan)-4-methoxy-4-(3''-phosphoryloxy)phenyl-1,2-dioxetane disodium salt (AMPPD) was added, and the enzymatic reaction was allowed to proceed at 37° C. for 4 minutes. The amount of chemiluminescence after the reaction was measured using a luminometer. As the measuring apparatus, a fully automated chemiluminescence immunoassay apparatus Lumipulse Presto II (manufactured by Fujirebio Inc.) was used.

Table 1 shows the results obtained by subjecting 9 serum/plasma paired samples to the measurement using the ALP-labeled anti-prothrombin polyclonal antibody as the enzyme-labeled antibody. Table 2 shows the results obtained by subjecting 9 serum/plasma paired samples to the measurement using a mixture of the ALP-labeled anti-F1 antibody (hPTN7-2 antibody) and the ALP-labeled anti-F2 antibody (20B8 antibody) as the enzyme-labeled antibody. As a result, as shown in Table 1, in the case where the ALP-labeled anti-prothrombin polyclonal antibody was used, the plasma/serum ratio observed for the heparin plasma was about 79% on average. Thus, it was confirmed that the serum-plasma correlation was low in this case. On the other hand, as shown in Table 2, in the case where the anti-F1 antibody and the anti-F2 antibody were mixed at a weight ratio of 2:1 was used as the ALP-labeled antibody, the plasma/serum ratio observed for the heparin plasma was about 102%, and the plasma/serum ratio observed for the EDTA plasma was about 105%. Thus, both samples showed improved serum-plasma correlation.

TABLE 1

|  | | Sample Type | |
| --- | --- | --- | --- |
|  | Sample No. | Serum | Heparin Plasma |
| Measured Value mAU/mL | 1 | 15.5 | 12.6 |
|  | 2 | 17.4 | 13.8 |
|  | 3 | 15.9 | 11.5 |
|  | 4 | 20.8 | 16.3 |
|  | 5 | 15.9 | 13.9 |
|  | 6 | 19.1 | 16.1 |
|  | 7 | 24.6 | 17.1 |
|  | 8 | 19.6 | 15.4 |
|  | 9 | 15.2 | 11.9 |
| Ratio to Serum | 1 |  | 81% |
|  | 2 |  | 79% |
|  | 3 |  | 72% |
|  | 4 |  | 78% |
|  | 5 |  | 87% |
|  | 6 |  | 84% |
|  | 7 |  | 70% |
|  | 8 |  | 79% |
|  | 9 |  | 78% |
| Mean |  |  | 79% |

TABLE 2

|  | | Sample Type | | |
| --- | --- | --- | --- | --- |
|  | Sample No. | Serum | Heparin Plasma | EDTA Plasma |
| Measured Value mAU/mL | 1 | 15.1 | 15.5 | 15.5 |
|  | 2 | 16.6 | 16.9 | 18.3 |
|  | 3 | 13.9 | 13.6 | 14.1 |
|  | 4 | 19.4 | 21.3 | 21.0 |
|  | 5 | 15.9 | 15.6 | 16.9 |
|  | 6 | 20.0 | 20.1 | 19.9 |
|  | 7 | 21.0 | 21.3 | 21.0 |
|  | 8 | 18.9 | 18.4 | 19.6 |
|  | 9 | 14.1 | 14.9 | 16.4 |
| Ratio to Serum | 1 |  | 103% | 103% |
|  | 2 |  | 102% | 110% |
|  | 3 |  | 98% | 101% |
|  | 4 |  | 110% | 108% |
|  | 5 |  | 98% | 106% |
|  | 6 |  | 101% | 100% |

TABLE 2-continued

| | Sample Type | | |
|---|---|---|---|
| Sample No. | Serum | Heparin Plasma | EDTA Plasma |
| 7 | | 101% | 100% |
| 8 | | 97% | 104% |
| 9 | | 106% | 116% |
| Mean | | 102% | 105% |

Table 3 shows the results obtained by measuring PIVKA-II in 10 serum/plasma paired samples using as the anti-F1 antibody the PT5-23 antibody instead of the hPTN7-2 antibody and thus using as the enzyme-labeled antibody a 2:1 mixture of the ALP-labeled anti-F1 antibody (PT5-23 antibody) and the ALP-labeled anti-F2 antibody (20B8 antibody). When PT5-23 antibody was used as the ALP-labeled anti-F1 antibody in the form of a mixture with the ALP-labeled anti-F2 antibody, the plasma/serum ratio observed for the heparin plasma was about 106%, and the plasma/serum ratio observed for the EDTA plasma was about 107%. Thus, it was confirmed that good serum-plasma correlation could also be obtained for both plasma when using PT5-23 antibody.

TABLE 3

| | | Sample Type | | |
|---|---|---|---|---|
| | Sample No. | Serum | Heparin Plasma | EDTA Plasma |
| Measured Value mAU/mL | 13 | 17.1 | 17.7 | 18.5 |
| | 14 | 19.5 | 20.7 | 22.2 |
| | 15 | 16.3 | 17.3 | 16.1 |
| | 16 | 22.5 | 24.2 | 24.7 |
| | 17 | 18.8 | 19.8 | 20.2 |
| | 18 | 23.7 | 25.4 | 24.9 |

TABLE 3-continued

| | | Sample Type | | |
|---|---|---|---|---|
| | Sample No. | Serum | Heparin Plasma | EDTA Plasma |
| | 19 | 17.7 | 18.8 | 19.2 |
| | 20 | 25.2 | 26.0 | 26.2 |
| | 21 | 22.9 | 24.6 | 24.6 |
| | 22 | 17.4 | 17.5 | 19.2 |
| Ratio to Serum | 13 | | 104% | 108% |
| | 14 | | 106% | 114% |
| | 15 | | 106% | 99% |
| | 16 | | 108% | 110% |
| | 17 | | 105% | 107% |
| | 18 | | 107% | 105% |
| | 19 | | 106% | 108% |
| | 20 | | 103% | 104% |
| | 21 | | 107% | 107% |
| | 22 | | 101% | 110% |
| | Mean | | 106% | 107% |

(E) Study on Mixing Ratio

The mixing ratio between the ALP-labeled anti-F1 antibody and the ALP-labeled anti-F2 antibody was studied. As shown in Table 4, in the cases where 1.5 µg/mL anti-F2 antibody alone was added as the labeled antibody, the plasma/serum ratio was about 118%, and, in the cases where 0.5 µg/mL anti-F2 antibody alone was added, the plasma/serum ratio was about 127%. Thus, very high ratios were observed. In the cases where 1.5 µg/mL anti-F1 antibody alone was added as the labeled antibody, a very low plasma/serum ratio, about 68%, was observed. Thus, it was found that use of the anti-F1 antibody or anti-F2 antibody alone results in low serum-plasma correlation. On the other hand, in the cases where the anti-F1 antibody and the anti-F2 antibody were mixed, all cases studied at mixing ratios of 2:1 to 1:2 showed plasma/serum ratios of about 98% to about 110%. Thus, good serum-plasma correlation could be found.

TABLE 4

| ALP-Labeled Antibody(µg/mL) | 20B8 | 1.5 | | 0.5 | | 0.5 | | 0.5 | | 0.5 | | 0 | |
| | hPTN7-2 | 0 | | 0 | | 0.25 | | 0.5 | | 1 | | 1.5 | |
| Sample Type | | Serum | Heparin Plasma | Serum | Heparin Plasma | Serum | Heparin Plasma | Serum | Heparin Plasma | Serum | Heparin Plasma | Serum | Heparin Plasma |
| Measured Value (mAU/mL) | No. 10 | 29.0 | 32.0 | 30.0 | 35.0 | 23.0 | 25.0 | 22.0 | 21.0 | 21.0 | 21.0 | 15.0 | 10.0 |
| | No. 11 | 18.0 | 23.0 | 19.0 | 25.0 | 16.0 | 18.0 | 15.0 | 16.0 | 12.3 | 12.1 | 12.0 | 9.0 |
| | No. 12 | 27.0 | 31.0 | 27.0 | 36.0 | 23.0 | 25.0 | 21.0 | 22.0 | 20.0 | 19.0 | 16.0 | 10.0 |
| Ratio to Serum | No. 10 | | 110% | | 117% | | 109% | | 95% | | 100% | | 67% |
| | No. 11 | | 128% | | 132% | | 113% | | 107% | | 98% | | 75% |
| | No. 12 | | 115% | | 133% | | 109% | | 105% | | 95% | | 63% |
| | Mean | | 118% | | 127% | | 110% | | 102% | | 98% | | 68% |

The invention claimed is:

1. A method for measuring Protein Induced by Vitamin K Absence or Antagonist-II (PIVKA-II), comprising:
   measuring PIVKA-II in a sample by carrying out an immunoassay using antibodies comprising (a) an anti-PIVKA-II antibody that specifically binds to PIVKA-II or an antigen-binding fragment thereof and (b) a mixture of (i) an anti-F1 antibody that specifically binds to prothrombin fragment 1 or an antigen-binding fragment thereof and (ii) an anti-F2 antibody that specifically binds to prothrombin fragment 2 or an antigen-binding fragment thereof,
   wherein said anti-F1 antibody, said anti-F2 antibody, and said anti-PIVKA-II antibody are monoclonal antibodies,
   wherein the mixture of the anti-F1 antibody and the anti-F2 antibody is in a mixing ratio of 1:0.2-2,
   wherein the immunoassay is a sandwich immunoassay using said mixture as a labeled antibody and said anti-PIVKA-II antibody as an immobilized antibody, or using said mixture as an immobilized antibody and said anti-PIVKA-II antibody as the labeled antibody, and
   wherein said sample is serum or plasma.

2. The method according to claim 1, wherein said anti-F1 antibody is an antibody that recognizes an epitope in the F1 region and binds to PIVKA-II, and said anti-F2 antibody is an antibody that recognizes an epitope in the F2 region and binds to PIVKA-II.

3. The method according to claim 1, wherein said immunoassay is carried out by a sandwich method using said mixture as a labeled antibody and said anti-PIVKA-II antibody or antigen-binding fragment thereof as an immobilized antibody.

4. The method according to claim 1, wherein the mixture ratio between said anti-F1 antibody or the antigen-binding fragment thereof and said anti-F2 antibody or the antigen-binding fragment thereof is a weight ratio of 1:0.5-1.0.

5. The method according to claim 1, wherein said immunoassay has a serum-plasma ratio of 95% to 113%.

6. The method according to claim 1, wherein the mixture of the anti-F1 antibody and the anti-F2 antibody is in a mixing ratio of 1:0.2-0.5.

* * * * *